Figure 1:
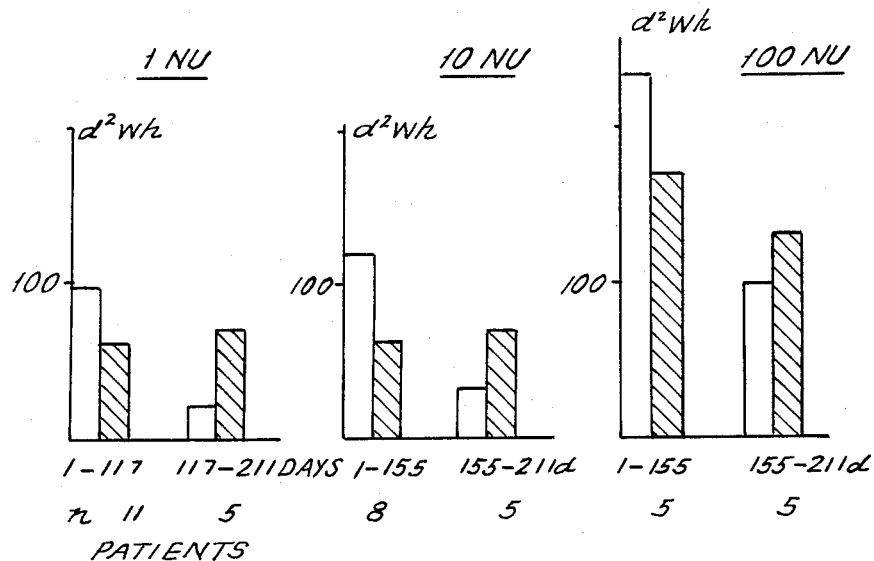

United States Patent [19]

Stevens et al.

[11] Patent Number: 4,600,583
[45] Date of Patent: Jul. 15, 1986

[54] PHARMACEUTICAL COMPOSITIONS

[75] Inventors: Erik Stevens, Linden-Lubbeek; Ernestina M. Van Hoeyveld, Lubbeek, both of Belgium

[73] Assignee: Tetra Consultants Inc., New Rochelle, N.Y.

[21] Appl. No.: 415,569

[22] Filed: Sep. 7, 1982

[51] Int. Cl.$^4$ .................. A61K 39/36; A61K 39/00
[52] U.S. Cl. ........................... 424/91; 424/88; 514/2; 514/561; 514/169; 514/226; 514/368; 514/615
[58] Field of Search ............... 424/88, 91, 85, 181, 424/246, 305, 311, 319, 320, 89; 252/403; 514/2, 561, 169, 226, 369, 615

[56] References Cited

U.S. PATENT DOCUMENTS

| | | | |
|---|---|---|---|
| 2,399,443 | 4/1946 | Masucci | 424/319 |
| 2,528,972 | 11/1950 | Pillemer | 424/319 |
| 3,146,164 | 8/1964 | Macek et al. | 424/181 |
| 3,541,201 | 11/1970 | Brown | 424/91 X |
| 3,594,471 | 7/1971 | Hertzberger | 424/89 |
| 4,221,906 | 9/1980 | Querry et al. | 424/181 X |
| 4,226,853 | 10/1986 | Marsh | 424/88 |
| 4,258,029 | 3/1981 | Maloney et al. | 424/88 |
| 4,496,537 | 1/1985 | Kwan | 424/85 |

FOREIGN PATENT DOCUMENTS 1250966 9/1967 Fed. Rep. of Germany ........ 424/85
2125038 12/1971 Fed. Rep. of Germany ...... 252/403

Primary Examiner—David M. Naff
Assistant Examiner—Shawn P. Foley

[57] ABSTRACT

The method of improving the storage stability of parenterally administerable physiologically active compositions which comprises, incorporating in said compositions a small but effective amount of a compound of the formulae,

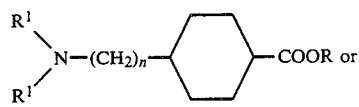

or

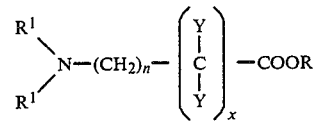

wherein R is H, lower alkyl or acyl; each $R^1$ is H or lower alkyl; and n is an integer of from 1 to 6; x is 0 or 1; each Y is H; and the non-toxic pharmaceutically acceptable salts thereof.

10 Claims, 2 Drawing Figures

TABLE 1

TABLE 2

PHARMACEUTICAL COMPOSITIONS

It has historically been widely recognized that various physiologically active compositions which are designed for parenteral administration to patients are susceptible to rapid deterioration. This is especially true in the case of those physiologically active compositions which are in the form of a liquid parenterally administerable composition. The deterioration of these parenterally administerable physiological compositions results in loss of potency or degradation of the physiologically active components thereof. This storage instability and the resulting degradation of the physiologically active components of these compositions is most prevalent in those parenterally administerable compositions which employ an aqueous vehicle.

In the past, this serious disadvantage of the degradation and storage instability of the liquid parenterally administerable physiologically active compositions has been sought to be overcome by various means, none of which have proven to be completely satisfactory.

Heretofore, many attempts have been made to solve this instability problem, most of which involve the incorporation into the parenterally administerable composition of substantial amounts of various agents which were supposed to obviate the problem. Among the various agents which have been employed for this purpose may be included such materials as glycerin; polysorbate 80 (polyoxyethylene (20) sorbitan monooleate); dextrose; human serum albumin; aluminum precipitation; siliconization of the vials used to store the compositions; buffered saline solutions, for example, phosphate- or bicarbonate-buffered; and various other materials, for example, polyvinyl pyrrolidone or polyethylene glycol. To date none of the foregoing has provided the satisfactory results required.

We have now discovered that the disadvantages suffered by the prior art parenterally administerable physiologically active compositions may be overcome by the practice of the instant invention. We have found that the storage stability of liquid, parenterally administerable, physiologically active compositions may be vastly improved by the incorporation therein of a small but effective amount of a compound selected from the group consisting of compounds of the formulae:

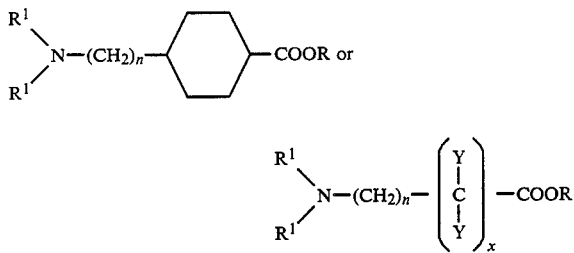

wherein $R^1$ is H or lower alkyl; n is an integer from 1 to 6; x is 0 or 1; each Y is H; and R is H, lower alkyl or acyl, and the non-toxic pharmaceutically acceptable salts thereof.

Most preferably, we have found that most satisfactory results are obtained when the liquid, parenterally administerable physiologically active compositions which are the subject of this invention have incorporated therein a small but effective amount of epsilon-aminocaproic acid or tranexamic acid; although the other compounds also provide acceptable results.

The compounds of this invention have been found to provide satisfactory results when incorporated into the subject liquid parenterally administerable, physiologically active compositions in small but effective amounts. We have found that the amounts of the compounds which may be employed herein should be sufficient to provide a final concentration thereof in the liquid, parenterally administerable, physiologically active composition to be administered to the patient, of from about 0.001M to about 0.5M. Preferably, in the practice of this invention the compounds of Formulae I may be present in the final, liquid, parenterally administerable, physiologically active compositions of this invention in a concentration of from about 0.001M to about 0.5M, and most preferably in a concentration of from about 0.1M to about 0.25M, although the other concentrations also provide satisfactory results.

The parenterally administerable, physiologically active compositions which may be employed in the practice of this invention include those parenterally administerable compositions which are stored and/or administered to the patient being treated in liquid form, and which are subject to deterioration, degradation or loss of potency on standing. More particularly, the compositions which may be employed in the practice of this invention are those which are in liquid form, for example, solutions, suspensions or mixtures, where the liquid vehicle is one which is a pharmaceutically acceptable liquid vehicle for parenteral administration, for example, water, oil, alcohol or the like, and which contains a physiologically active agent which is to be parenterally administered to the patient being treated. Parenteral administration of the final compositions of this invention may be accomplished by the administration thereof by any of the following routes: subcataneous, intradermal, intramuscular, intravenous or any other parenteral route ususally employed for this purpose by the skilled worker employing whatever means are commonly used for such purposes, for example, hypodermic needle and syringe, and the like.

The physiologically active substances which may be employed in the practice of this invention are those substances which are to be parenterally administered to the patient and include substances which are parenterally administered for either therapeutic or diagnostic purposes. The physiologically active substances which may be employed include those biologically active materials which may be of chemical or biological origin and include such substances as antibiotics, hormones, steroids, allergenic substances, allergen extracts, sera, toxins, anti-toxins, vaccines, and other like substances. Preferably, in the practice of the instant invention it is desired to employ those physiologically active substances which are derived from biological sources for example, antibiotics, allergenic materials and extracts, biological extracts, for example, vaccines, sera, and anti-toxins, for it has been determined that such biologically originated materials are most susceptible to storage instability and degradation. The amounts of the physiologically active substances which may be employed in the practice of this invention are those which are normally administered to the patients for the condition being treated or the purpose required, and will depend on the factors usually determined by the skilled worker to control the amounts of the substance being employed.

The final compositions of this invention may be prepared in any manner considered suitable by the skilled worker practicing the invention. The individual components of the final compositions of this invention may be admixed to form the desired compositions, or in some instances where the physiologically active substance is in a dry state, for example, as a result of lyophilization, the said physiologically active substance may first be reconstituted by the addition of the desired liquid vehicle, for example, water, and the required amounts of the compounds of Formulae(I) then incorporated, for example, by admixing, to yield the final storageably stable final compositions of this invention. The thus storageably stable final compositions may then be held for example, be being in a frozen state, or stored at ambient temperatures, for future use, with significant inhibitor or the normal degradation or deterioration which might otherwise adversely affect either the purity, efficacy or potency of the final compositions.

The term "alkyl" as employed herein shall mean and include those alkyl moieties generally considered lower alkyl groups which contain six or less carbon atoms. The acyl moreties which may be employed in the practice of the instant invention include those acyl groups derived from hydrocarbon carboxylic acids of twelve carbon atoms or less, such as, alkanoic acids, cycloalkanoic acids, monocyclic aryl carboxylic acids and the like.

The invention may be further illustrated by the following examples:

EXAMPLE 1

Grass pollen extract (*Lolium perenne*) (commercially available from HAL Allergenen Laboratorium B. V., Haarlem, Holland) was admixed with 10 ml. of pyrogen-free, distilled water. To the resultant solution was added with mixing, epsilon-aminocaproic acid until the resultant concentration thereof in the final solution was 0.1M. The resultant final composition was then divided into individual parenterally administerable doses of 0.05 ml. each.

EXAMPLE 2

The procedure of Example 1 was followed except that an equivalent amount of house dust mite extract (commercially available from HAL Allergenen Laboratorium B.V.) was substituted for the grass pollen extract, yielding equivalent results.

EXAMPLE 3

The procedure of Example 1 may be followed except that an equivalent amount of tranexamic acid may be substituted for epsilon-aminocaproic acid, with like results.

EXAMPLE 4

The procedure of Example 1 may be followed except that equivalent amounts of antibiotics, for example, penicillin G, cephalosporin, tetracycline or oxytetracycline; vaccines, for example, pertussis, typhoid, antirabies, or yellow fever vaccine; anti-toxin, for example, tetanus anti-toxin, may be substituted for the grass pollen extract, with similar results.

EXAMPLE 5

In vivo tests were performed employing the parenteral compositions of this invention. Grass pollen allergen extract and house dust mite allergen extracts were prepared in accordance with the procedures set forth in Example 1. In addition, as controls, compositions were prepared in accordance with the procedures of Example 1 and 2, except that sodium phosphate was substituted for epsilon-aminocaproic acid to a concentration of 0.15M.

The final parenterally administerable extracts had the following compositions:

A. Grass pollen allergens in pyrogen-free distilled water containing 0.1M epsilon-aminocaproic acid.

B. Grass pollen allergens in pyrogen-free distilled water containing 0.15M sodium phosphate.

C. House dust mite allergens in pyrogen-free distilled water containing 0.1M epsilon-aminocaproic acid.

D. House dust mite allergens in pyrogen-free distilled water containing 0.15M sodium phosphate.

Figure 2:
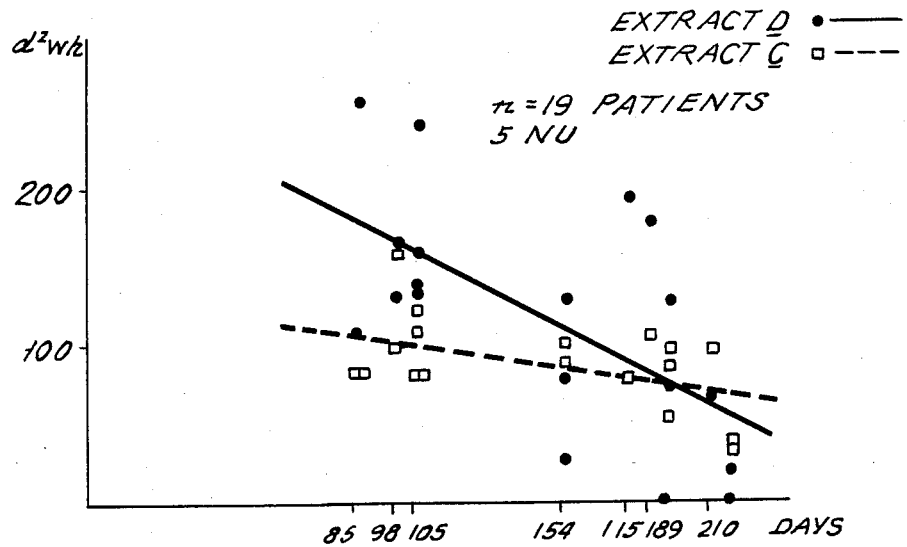

Final extract compositions were prepared to provide Compositions A and B with grass pollen allergen concentrations of 1, 10 and 100 Noon Units per 0.05 ml. respectively, and Compositions C and D with a house dust mite allergen concentration of 5 Noon Units per 0.05 ml. The final extract compositions (0.05 ml.) were intradermally injected into the test subjects' forearms at various sites at premeasured distances from each other over an extended period of time after preparation. In the case of Compositions A and B, these tests were made over a period of 211 days after preparation of the compositions; and in the case of Compositions C and D, over 210 days after preparation. Each skin test was read fifteen minutes after the administration thereof. The wheal and flare reactions which is a measure of the potency of the extract composition's allergenicity, were delineated on a transparent sheet and the mean square wheal diameters ($d^2wh$) were calculated. The results set forth in FIGS. 1 and 2 demonstrate that while there is a consistent and persistant degradation in the potency of prior art compositions, the compositions of this invention have little or no potency loss over an extended period of time.

EXAMPLE 6

In vitro experiments were performed to demonstrate the improved storage stability of the compositions of the instant invention. A grass pollen extract (*Lolium perenne*) containing 50,000 NU in 50% glycerol was held at −70° C. until diluted from 2000 NU in a series of dilutions down to 31 NU, in the following compositions:

A. Grass pollen with 0.154M phenolated phosphate, pH=7.

B. Grass pollen with phenolated phosphate containing 0.1M epsilon-aminocaproic acid.

Allergen coupled cellulose discs were made in accordance with the RAST method (A.B. Pharmacia, Sweden) using a bicarbonate buffered *Lolium perenne* extract. A RAST positive sera was used in RAST inhibition tests which were performed on the subject compositions to determine their activity. The results which demonstrate the reduction in the degradation by freezing and thawing of the instant compositions are set forth in Table 1.

TABLE 1

| | Relative Activity | | |
|---|---|---|---|
| Extract A | 1.0 | 1.0 | 1.0 |
| Extract B | 1.6 | 1.5 | 1.7 |

The above results demonstrate the relative activity of Extract B compared to Extract A and show that the activity of Extract B is substantially greater than that of Extract A.

EXAMPLE 7

The extract compositions prepared in Example 6 and containing 2000 NU of grass pollen allergens were then divided into 5 equal portions. One portion was employed as a control and the other four portions were incubated for 6, 24, 48 hours and 7 days respectively, at 37° C. At the end of each time period the test composition was tested in accordance with the RAST inhibition method to determine the relative potencies thereof. The results, which show that the compositions of this invention are more potent than those of the prior art, are set forth in Table 2 below.

TABLE 2

|  | RAST Potencies After: | | | | |
|---|---|---|---|---|---|
|  | 0 Hrs. | 6 Hrs. | 1 Day | 2 Days | 7 Days |
| Extract A | 1.0 | 0.70 | 0.42 | 0.41 | 0.14 |
| Extract B | 1.0 | 0.94 | 0.65 | 0.52 | 0.22 |

These results demonstrate that the shelf life of Extract B is approximately twice that of Extract A.

EXAMPLE 8

The procedure of Example 7 was repeated except that the extracts were stored at a temperature of 4° C. for 1, 3 and 6 months. The results obtained are set forth in Table 3.

TABLE 3

|  | RAST Potencies After: | | | |
|---|---|---|---|---|
|  | 0 Month | 1 Month | 2 Months | 3 Months |
| Extract A | 1.0 | 0.77 | 0.55 | 0.36 |
| Extract B | 1.0 | 0.57 | 0.32 | 0.26 |

The foregoing results demonstrate that the shelf life of Extract B is approximately three times that of Extract A.

The invention may be otherwise embodied within the scope of the appended claims.

What is claimed is:

1. In a composition for parenteral administration comprised of physiologically active substances selected from the group consisting of antibiotics, hormones, steroids, allergenic substances, allergen extracts, toxins and antitoxins, wherein the improvement comprises having incorporated therein an effective amount of a compound selected from the group consisting of:

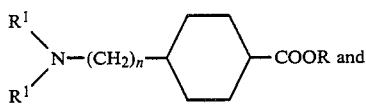

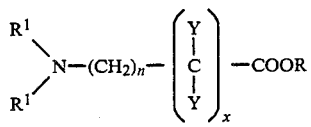

wherein R is H, lower alkyl or acyl; x is 0 or 1; each Y is H; $R^1$ is H or lower alkyl; and n is an integer of from 1 to 6; and the non-toxic pharmaceutically acceptable salts thereof, wherein the effective amount imparts storage stability.

2. The composition of claim 1 wherein the compound is epsilonaminocaproic acid.

3. The composition of claim 1 wherein the physiologically active composition is an allergenic extract.

4. In a method of preparing a composition for parenteral administration comprised of physiologically active substances selected from the group consisting of antibiotics, hormones, steroids, allergenic substances, allergen extracts, toxins and antitoxins, wherein the improvement comprises the addition of an effective amount of a compound selected from the group consisting of:

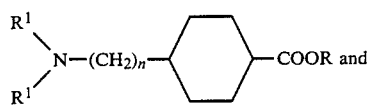

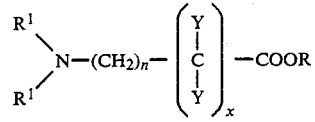

wherein R is H, lower alkyl or acyl; x is 0 or 1; each Y is H; $R^1$ is H or lower alkyl; and n is an integer of from 1 to 6; and the non-toxic pharmaceutically acceptable salts thereof for the purposes of storage stability.

5. The method of claim 4 wherein the compound is epsilonaminocaproic acid.

6. The method of claim 4 wherein the physiologically active composition is an allergenic extract.

7. In a composition for parenteral administration comprised of physiologically active substances selected from the group consisting of allergenic substances and allergen extracts, wherein the improvement comprises having incorporated therein an effective amount of a compound selected from the group consisting of:

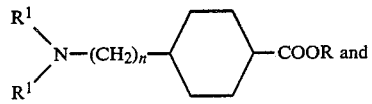

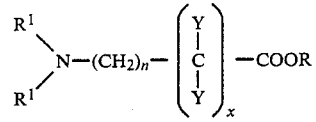

wherein R is H, lower alkyl or acyl; x is 0 or 1; each Y is H; $R^1$ is H or lower alkyl; and n is an integer of from 1 to 6; and the non-toxic pharmaceutically acceptable salts thereof, wherein the effective amount imparts storage stability.

8. The composition of claim 8 wherein the compound is present in the final parenterally administerable composition in a concentration of from about 0.001M to about 0.5M thereof.

9. The composition of claim 8 wherein the compound is present in the final parenterally administerable composition in a concentration of from about 0.1M to about 0.25M.

10. In a method of preparing a compositions for parenteral administration comprised of physiologically active substances selected from the group consisting of antibiotics, hormones, steroids, allergenic substances, allergen extracts, toxins and antitoxins, wherein the improvement comprises the addition of an effective amount of tranexamic acid and the non-toxic pharmaceutically acceptable salts thereof for the purposes of storage stability.

* * * * *